United States Patent [19]

Johnson

[11] Patent Number: 5,116,337

[45] Date of Patent: May 26, 1992

[54] FIXATION SCREW AND METHOD FOR LIGAMENT RECONSTRUCTION

[76] Inventor: Lanny L. Johnson, 3800 Hagadorn Rd., Okemos, Mich. 48864

[21] Appl. No.: 721,893

[22] Filed: Jun. 27, 1991

[51] Int. Cl.$^5$ ............................................. A61B 17/58
[52] U.S. Cl. ...................................... 606/73; 606/60; 411/178; 411/407; 411/412; 411/436
[58] Field of Search ................ 606/60, 65, 72, 73; 411/412, 413, 178, 436, 427, 393, 403, 407, 410

[56] References Cited

U.S. PATENT DOCUMENTS

| | | | |
|---|---|---|---|
| 24,855 | 11/1895 | Trapp | 359/467 |
| Re. 33,348 | 10/1990 | Lower | 606/65 |
| D. 225,970 | 1/1973 | O'Donnell | D8/267 |
| D. 296,362 | 6/1988 | Branemark | D24/33 |
| 1,007,107 | 10/1911 | Halsmann | 411/407 X |
| 2,112,007 | 3/1938 | Adams | 433/174 |
| 3,554,193 | 1/1971 | Konstantinou | 606/65 |
| 3,744,488 | 7/1973 | Cox | 606/64 |
| 3,987,499 | 8/1974 | Scharbach et al. | 623/17 |
| 4,259,072 | 3/1981 | Hirabayashi et al. | 433/173 |
| 4,468,200 | 8/1984 | Munch | 433/174 |
| 4,537,185 | 8/1985 | Stednitz | 606/73 |
| 4,636,125 | 1/1987 | Burgard | 411/410 X |
| 4,818,165 | 4/1989 | Shirai | 411/178 |
| 4,870,957 | 10/1989 | Goble et al. | 606/73 |
| 5,030,052 | 7/1991 | Anderson et al. | 411/412 X |
| 5,032,125 | 7/1991 | Durham et al. | 606/73 X |

FOREIGN PATENT DOCUMENTS 501548  3/1939  United Kingdom ............... 411/403

OTHER PUBLICATIONS

Kenneth L. Lambert, M.D., Vascularized Patellar Tendon Graft with Rigid Internal Fixation for Anterior Cruciate Ligament Insufficiency, Patellar Tendon Graft, Jan., Feb. 1983 No. 172, pp. 85-88.
Bernard R. Bach, Jr., M.D., Potential Pitfalls of Kurosaka Screw Interference Fixation for ACL Surgery, Sports Medicine Section, Dept. of Orthopedic Surgery, Rush-Presbyterian-St. Luke's Medical Center, Chicago, pp. 76-82.
Bernard R. Bach, Jr., M.D., Arthroscopy-Assisted Patellar Tendon Substitution for Anterior Cruciate Ligament Insufficiency, Sports Medicine Section, Dept. of Orthopedic Surgery, Rush-Presbyterian-St. Luke's Medical Center, Chicago, pp. 3-20.
Erik Oberg, Franklin D. Jones and Holbrook L. Horton, Machinery's Handbook, Twenty First Edition, 1980 pp. 1136, 1207, 1348 and 1374.
Excerpts from Physicians' Current Procedural Terminology, 1990, p. 125.
When It Comes to ACL, Why Screw Around With Anyone Else, ACUFEX Advertisement, 1990.

Primary Examiner—Robert A. Hafer
Assistant Examiner—Kevin G. Rooney
Attorney, Agent, or Firm—Cushman, Darby & Cushman

[57] ABSTRACT

A screw for fixation of a tendon/bone graft during an arthroscopic surgical procedure includes a smooth conical forward end having a rounded tip and a spiral thread running from a position behind the smooth rounded forward end to a rearward end of the screw. The depth of the thread is shallower than a conventional screw and the exterior edge of the thread is rounded to decrease cutting and fragmentation of the tendon and bone. The screw includes an internal bore with left- and right-handed threaded portions for engagement with insertion and extraction instruments. In the method, the bone graft is harvested and sized as desired. A graft socket is drilled in the bone and then serially sized with increasingly larger sizing instruments to compact the bone and size the graft socket to the graft. A smooth bore screw socket is created by serially dilating a space between the graft and graft socket with increasingly larger dilating instruments, thereby also compacting the graft. The appropriately sized fixation screw is then inserted into the screw socket with the insertion instrument to fix the graft to the bone.

4 Claims, 2 Drawing Sheets

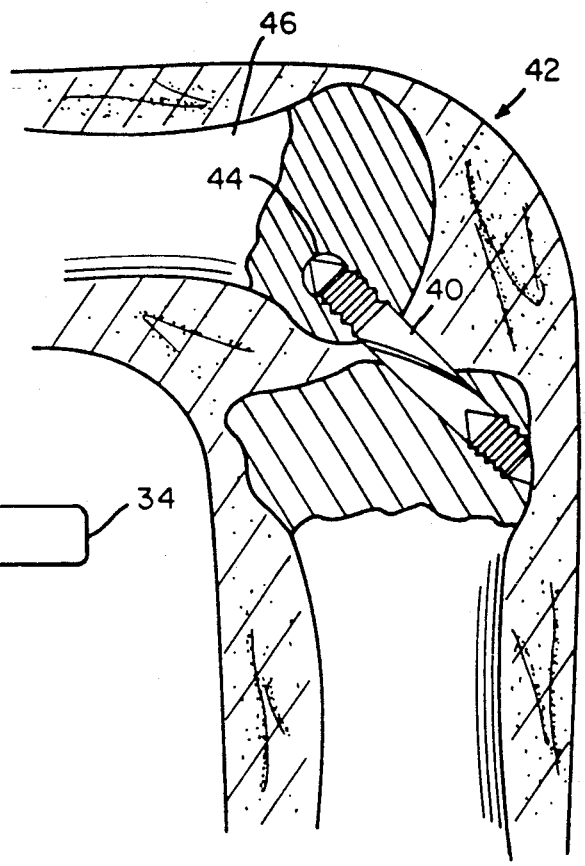
FIG. 4
FIG. 5
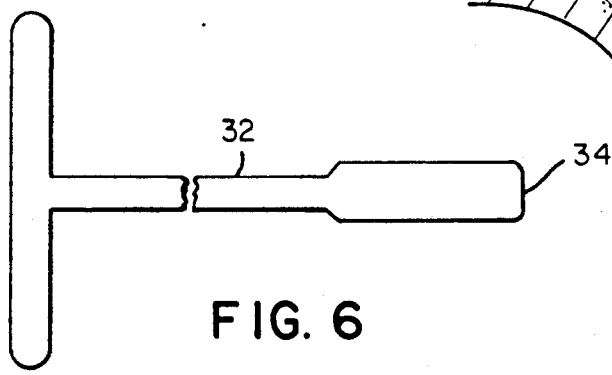
FIG. 6
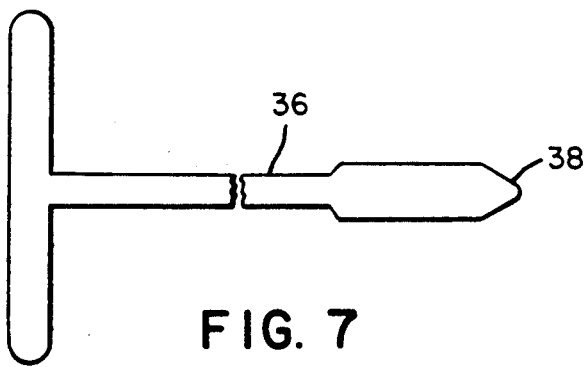
FIG. 7

FIXATION SCREW AND METHOD FOR LIGAMENT RECONSTRUCTION

BACKGROUND OF THE INVENTION

1. Field of the Invention

The present invention relates to a screw for fixation of a bone/tendon graft during a surgical procedure and particularly, to arthroscopic anterior cruciate ligament reconstruction.

2. Related Art

Ligament reconstruction by replacing the ligament with a tendon/bone graft is well known in the art. For instance, during arthroscopic knee surgery, a surgeon can form a tunnel through the tibia, intra articular joint and femur to receive a bone-tendon-bone graft harvested from the patellar tendon. A variety of techniques have been employed to secure the bone-tendon-bone graft, such as tying sutures over ligament buttons, staples, unicortical screw posts, or interference screws. An example of one such ligament anchor system is disclosed in U.S. Pat. No. 4,870,957, which is incorporated by reference herein.

One common example of interference screw is the self-tapping Kurosaka screw which cuts its own threads into the bone and graft. With this type of screw, the graft bone plug is sized to be smaller than the receptive bone tunnel to provide clearance for the screw to begin self-tapping and threading. However, there are many disadvantages to such types of screws. Since there is no preformed channel for the screw to enter, but rather, the screw cuts its own channel within the clearance between the bone and the graft, the screw can diverge, reducing screw thread to bone plug contact. The self-tapping operation cuts into the graft, thereby possibly causing graft damage or fragmentation. The insertion of the screw can also cause migration or translocation of the graft.

Further, the Kurosaka type screw is not well secured to the insertion device and can fall off the insertion device as well as require a K-wire insertion. The bone tunnel is usually created with an acorn type drill head which can cause cavitation of the tunnel wall and the depth of the tunnel is not controlled.

SUMMARY OF THE INVENTION

The preferred exemplary embodiment of the present invention includes a screw for fixation of a tendon/bone graft to a bone. The non-self-tapping, non-thread cutting screw includes a smooth conical forward end having a rounded tip. A right-handed spiral thread runs from a position behind the smooth rounded forward end to a rearward end of the screw. The depth of the thread is shallower than conventional interference screws and the thread has a rounded exterior edge to decrease cutting and fragmentation of the tendon and bone.

The screw includes an internal longitudinal bore with a right-handed threaded portion and a left-handed threaded portion having a smaller diameter than the right-handed threaded portion. An insertion device with a right-handed threaded portion can be engaged with the right-handed threaded portion of the screw bore to screw the screw into a prepared screw socket. A left-handed threaded extraction device can be engaged with the left-handed portion of the internal bore to extract the screw. The screw can be fixed by inserting a wire in a radial bore disposed in a rearward portion of the screw for removal of the insertion or extraction devices without disturbing the placement of the screw.

In the method for fixation of the tendon/bone graft, a bone-tendon-bone graft is harvested from the patellar tendon. Each bone plug of the bone-tendon-bone graft is harvested in a semicircular cross-section with a semicircular gouge and is conventionally sized. A graft socket is then drilled into the bone with an anti-cavitational drill. The bone surrounding the drilled socket is compacted by sizing the socket with a series of increasingly larger tubular sizing instruments until the compacted socket is sized to accommodate the bone plug.

The bone plug is then inserted into the compacted socket and positioned as desired. The bone plug may be held in place by a conventional K-wire or with sutures, if necessary. The bone plug is compacted into the compacted socket by inserting a series of increasingly larger tubular dilating instruments between the compacted socket and the bone plug, thereby forming a screw socket. After the largest dilating instrument has been used, the compacting of the socket and bone plug can be continued with the larger sizing instruments as discussed above. When the next larger size sizing instrument cannot be manually inserted into the screw socket, the screw size is chosen to be the same as the size of the compacted screw socket, i.e., the same size as the last dilating or sizing instrument that could be inserted into the screw socket.

The sized screw is then screwed onto the insertion tool, whereupon the screw is threaded into the screw socket, thereby securing the bone plug to the bone. If necessary, an extraction tool can be screwed into the left-handed threaded portion of the internal bore to extract the screw, either slightly or entirely. The same method is also carried out with the other bone plug of the bone-tendon-bone graft, with the method steps for fixing the two bone plugs overlapping. The remainder of the surgical operation proceeds conventionally.

Thus, the screw of the present invention enters a precreated unthreaded, smooth wall screw socket of compressed bone, thereby creating a maximum tight fit for the screw threads and a side-to-side compression fit between the bone plug and bone. The precreated screw socket prevents divergence of the screw and migration of the graft. Only the initial socket is drilled and threads are not cut into the bone or bone plug, thereby preventing cutting and fragmentation of the bone plug. Rather, the screw fixes the bone plug through the use of displacement and compression. The screw need not be made of expensive alloys but can be constructed of surgical stainless steel.

With the foregoing in mind, other objects, features and advantages of the present invention will become more apparent upon consideration of the following description and the appended claims with reference to the accompanying drawings, all of which form part of this specification, wherein like reference numerals designate corresponding parts in the various figures.

BRIEF DESCRIPTION OF THE DRAWINGS

FIG. 4 is a side elevational view of a patient's knee showing the fixation screws of the present invention fixing a bone-tendon-bone graft;

FIG. 5 is an end elevational view of the semicircular harvested bone plug;

FIG. 6 is a side elevational view of a sizing instrument; and

FIG. 7 is a side elevational view of a dilating instrument.

DESCRIPTION OF THE PREFERRED EXEMPLARY EMBODIMENT

Figure 1:
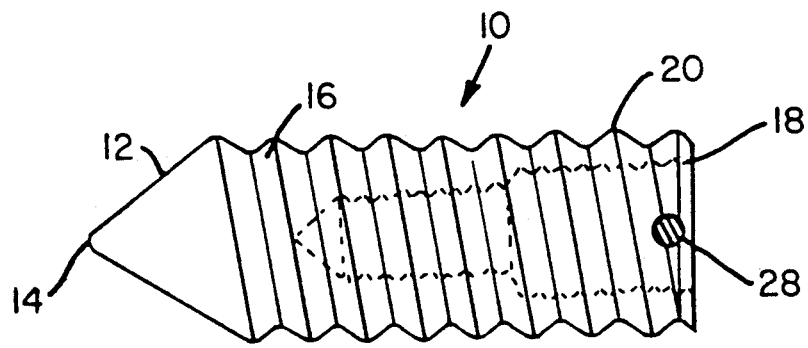
FIG. 1 is a side elevational view of the fixation screw of the present invention.
Figure 2:
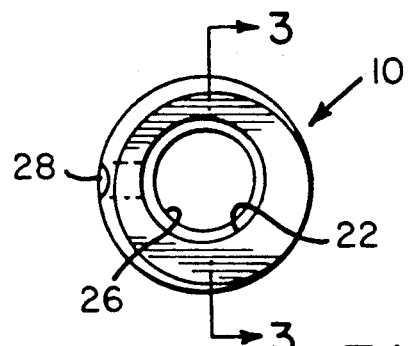
FIG. 2 is a rear elevational of the fixation screw.
Figure 3:
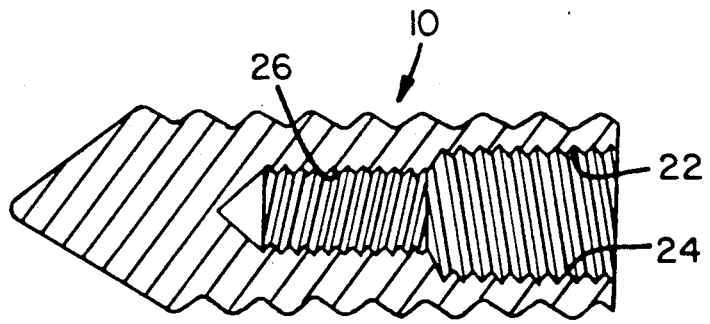
FIG. 3 is a sectional view taken along section line 3—3 of FIG. 2.

FIGS. 1-3 show a preferred embodiment of a fixation screw 10 according to the present invention. The screw has a smooth conical forward end 12 with a rounded tip 14 and is of a headless design. A right-handed spiral thread 16 runs from a position behind the smooth conical forward end 14 to a rearward end 18 of the screw 10. The depth of the thread 16 is shallower than conventional interference screws and the thread 16 has a rounded exterior edge 20 and root 21 to decrease cutting and fragmentation of the bone.

The screw includes an internal longitudinal bore 22 with a right-handed threaded portion 24 and a smaller diameter left-handed threaded portion 26 nearer the forward end 12. A right-handed threaded insertion device (not shown) can be engaged with the right-handed threaded portion 24 for screwing the fixation screw 10 into a prepared screw socket. A left-handed threaded insertion device (not shown) can be engaged with the left-handed threaded portion 26 for extraction of the screw 10. Of course, in an alternative embodiment, spiral thread 16 and threaded portion 24 can be left-handed while threaded portion 26 is right-handed.

The screw 10 further includes a radial bore 28 located near the rearward end 18. A wire (not shown) can be placed in the bore 28 to prevent rotation of the screw 10 while the insertion or extraction device is being removed from the screw 10. In the preferred embodiment, the screw 10 is made from surgical stainless steel and need not be made from an expensive alloy. Of course, other appropriate materials can also be used as well known in the art, including biodegradable material.

In the preferred embodiment, the screw 10 is 25 to 40 mm long and has 5 threads/inch, regardless of the outer diameter of the screw 10, which can be 5, 7, 9, 11 or 13 mm. The exterior edge 20 and root 21 are rounded to a 0.02 inch radius and the height of the thread 16 from root 21 to exterior edge 20 is 0.065 inch. The thread 16 does not extend diametrically beyond the largest outer diameter of the conical forward end 12. The forward end 12 has an angle of 28 degrees from a longitudinal axis of the screw to the exterior conical surface of the forward end 12. Threaded portion 24 has an 8-32 right-handed thread and threaded portion 26 has a 6-32 left-handed thread.

In the method for fixation of the tendon/bone graft, for instance, in arthroscopic reconstruction of the anterior cruciate ligament, a bone-tendon-bone graft is harvested from the patellar tendon, as conventionally known. Each bone plug 30 of the bone-tendon-bone graft is harvested in a semicircular cross-section, as shown in FIG. 5, with a semicircular gouge. Reference can also be made to FIG. 4 which shows the bone-tendon-bone graft 40 secured in a patient's knee 42 with the fixation screws 10. The size of the bone-tendon-bone graft is predetermined for each individual patient and in the preferred embodiments, a 9, 10 or 11 mm (and 12 and 13 mm) diameter semicircular bone plug 30 is harvested on each end of the bone-tendon-bone graft. Each bone plug is then conventionally shaped and sized to the desired dimensions.

Next, a blind graft socket 44 is drilled in the femur 46 with an anti-cavitational drill, which is provided in 8, 9, 10 and 11 mm diameters. The anti-cavitational drill does not have an acorn-type head that can drill out-of-round holes or cavitate the graft socket, thereby deteriorating the bone plug to graft socket fit. Rather, the drill has straight sides with a rounded tip. A through socket can also be drilled if desired or for a different application. The size of the drill is chosen to be smaller than the size of the bone plug 30. For instance, if the bone plug 30 is 11 mm, an 8 mm graft socket is initially drilled.

The bone surrounding the graft socket 44 is then compacted and the graft socket 44 enlarged and sized by manually inserting a sizing instrument 32 having a larger diameter than the selected drill into the graft socket 44. The sizing instrument 32 is shown in FIG. 6 and is tubular with a blunt forward end 34 having rounded edges. The sizing instrument 32 can also have a conical or other shape forward end in an alternative embodiment.

The sizing of the graft socket 44 is preferably done serially with increasingly larger sizing instruments 32 until the graft socket 44 has been sized to the size of the bone plug 30 and the surrounding bone has been firmly compacted. If the graft socket 44 cannot be sized large enough for the harvested bone plug 30, preferably the graft socket 44 would be redrilled with a larger drill and then resized, if necessary, as discussed above. This will depend on the hardness of the bone and the degree of compaction of the bone that can achieved. Alternatively, the bone plug 30 can be resized to be smaller to fit the sized graft socket 44.

The sized bone plug 30 of the bone-tendon-bone graft is then inserted into the sized graft socket 44 to the bottom of the graft socket 44 and positioned as desired. The placement of the bone-tendon-bone graft 40 can be eased with the use of a standard guide wire inserted into the graft. If necessary, the bone plug can be held in place by a conventional K-wire or with sutures. The bone plug 30 is compacted into the graft socket 44 with a smooth tubular dilating instrument 36 having a conical forward end 38, as shown in FIG. 7. In an alternative embodiment, the forward end 38 can be more blunt or more rounded or have another shape.

The dilating instrument is provided in 4, 5, 6, 7 and 8 mm sizes and is inserted into the cavity between the semicircular bone plug 30 and the graft socket 44 to compact the bone plug 30, further compact the graft socket 44 and to size a screw socket for receiving the fixation screw 10. As with the sizing of the graft socket 44, the compacting of the bone plug is done serially with increasingly larger diameter dilating instruments 36 and sizing instruments 32 until the desired diameter screw socket is achieved or until the next larger dilating instrument 36 or sizing instrument 34 cannot be manually inserted into the screw socket. Preferably, the screw socket is sized to be smaller in diameter than the sized bone plug 30. For instance, if a 10 mm bone plug is used, the screw socket would only be sized to 8 mm, for use with an 8 mm diameter screw 10. A screw having a larger-diameter than the screw socket can also be used, if even further compaction of the graft socket and bone plug is desired.

The screw 10 is then screwed onto the insertion device for insertion into the screw socket. The screw 10 is screwed into the screw socket until it bottoms, then is turned an additional small amount to make certain that everything is secure. If a blind graft socket was not used, then the screw 10 is screwed in until it reaches a desired position. The insertion device can then be removed from the screw 10. If necessary, a wire can be temporarily inserted into the radial bore 28 to secure the screw 10 while the insertion device is being removed. If extraction of the screw 10 is necessary, the extraction device can now be used.

The same method is used for the second bone plug 30 of the bone-tendon-bone graft 40, with the method steps for fixing the two bone plugs 30 overlapping. Any undiscussed portions of the surgical operation proceed conventionally. After 4 to 6 weeks there will be a bony union between the bone plugs and the femur and tibia, respectively, and the fixation screws will no longer have any function. The screws will not generally be removed at this time, although they can be.

Although the procedure discussed above is in reference to reconstruction of the anterior cruciate ligament, it should be realized that the screw and method of the present invention can be used in other ligament/tendon reconstructive applications, arthroscopic or otherwise. Further, the sizes of drills, screws, sizing instruments and dilating instruments can also be altered as necessary. The screws 10 and drills can be cannulated for use with a guide wire, as conventionally known.

While the invention has been described in accordance with what is presently conceived to be the most practical and preferred embodiment, it is to be understood that the invention is not to be limited to the disclosed embodiment but on the contrary, is intended to cover various modifications and equivalent arrangements included within the spirit and the scope of the appended claims, which scope is to be accorded the broadest interpretation of such claims so as to encompass all such equivalent structures.

What is claimed is:

1. A screw for fixation of a tendon/bone graft during a surgical procedure, comprising:
    a smooth conical forward end having a rounded tip,
    a spiral thread running from a position behind the smooth conical forward end to a rearward end of the screw, the depth of the thread being shallow and an exterior edge of the thread being rounded to decrease cutting and fragmentation of the tendon and bone,
    a longitudinal internal bore including a first right-handed threaded portion and a second left-handed threaded portion, one of the first and second threaded portions engageable with an insertion device for insertion of the screw, the other of the first and second threaded portions engageable with an extraction device for extraction of the screw, one of the first and second threaded portions having a smaller diameter than the other of the first and second threaded portions, the threaded portion with the smaller diameter being located closer to the forward end of the screw.

2. A screw as in claim 1, and further comprising at least one radial bore located near the rearward end of the screw for use in preventing rotation of the screw while at least one of the insertion device and the extraction device is being removed from the screw.

3. A screw as in claim 1, wherein the screw is headless.

4. A screw as in claim 1, wherein the screw is constructed of one of a surgical stainless steel and biodegradable materials.

* * * * *